(12) United States Patent
Kanda (10) Patent No.: US 8,358,412 B2
(45) Date of Patent: Jan. 22, 2013

(54) SYSTEM AND PROCESS FOR SORTING BIOLOGICAL PARTICLES IN LIQUID FLOW

(75) Inventor: Masahiko Kanda, Hyogo (JP)

(73) Assignee: Bay Bioscience Kabushiki Kaisha, Hyogo (JP)

( * ) Notice: Subject to any disclaimer, the term of this patent is extended or adjusted under 35 U.S.C. 154(b) by 300 days.

(21) Appl. No.: 12/735,044

(22) PCT Filed: Dec. 9, 2008

(86) PCT No.: PCT/JP2008/072308
§ 371 (c)(1),
(2), (4) Date: Jun. 11, 2010

(87) PCT Pub. No.: WO2009/078307
PCT Pub. Date: Jun. 25, 2009

(65) Prior Publication Data
US 2010/0297759 A1    Nov. 25, 2010

(30) Foreign Application Priority Data

Dec. 14, 2007  (JP) ................................. 2007-323225

(51) Int. Cl.
*G01N 21/00* (2006.01)
(52) U.S. Cl. ....................................................... 356/337
(58) Field of Classification Search .................. None
See application file for complete search history.

(56) References Cited

U.S. PATENT DOCUMENTS

| | | | |
|---|---|---|---|
| 5,540,494 A * | 7/1996 | Purvis et al. .................. 356/73 |
| 6,248,590 B1 | 6/2001 | Malachowski | |
| 6,589,792 B1 * | 7/2003 | Malachowski .................. 436/63 |
| 6,976,590 B2 * | 12/2005 | Deshpande et al. .......... 209/631 |
| 7,417,734 B2 | 8/2008 | Kanda | |
| 2007/0195310 A1 | 8/2007 | Kanda | |

FOREIGN PATENT DOCUMENTS

| | | |
|---|---|---|
| JP | 1990-150552 | 12/1990 |
| JP | 2005-315799 | 11/2005 |

OTHER PUBLICATIONS

Tomoyoshi Kumagai et al., "Study on Simple Determination of Delay Time for Charging Droplet in Cell Sorter", Proceedings of Annual Meeting of the Institute of Electrostatics Japan, Sep. 29, 1993, pp. 215-216.
International Search Report Mar. 17, 2009.
Tomoyoshi Kumagai et al., "Study on Simple Determination of Delay Time for Charging Droplet in Cell Sorter", Proceedings of Annual Meeting of the Institute of Electrostatics Japan, Sep. 29, 1993, pp. 215-216. (Corrected Translation provided).
International Search Report.

* cited by examiner

*Primary Examiner* — Tu Nguyen
(74) *Attorney, Agent, or Firm* — Harness, Dickey & Pierce, P.L.C.

(57) ABSTRACT

The embodiment of the present invention is to provide a system for sorting biological particles in a liquid flow, such as a cell sorter, which comprises an optical mechanism emitting laser beam onto each of the biological particles to detect light therefrom, a controller determining a moving speed of each of the biological particles in the liquid flow in accordance with the light detected therefrom, and an electric charger charging each of the biological particles based upon the moving speed thereof. Therefore, the cell sorter according to the embodiment of the present invention can improve recovery rate and purity of the desired cell particles.

25 Claims, 7 Drawing Sheets

Fig. 1 (Conventional)

SYSTEM AND PROCESS FOR SORTING BIOLOGICAL PARTICLES IN LIQUID FLOW

TECHNICAL FIELD

The present invention relates to a system and a process for collecting identification information of biological particles such as cells and chromosomes, and for analyzing and sorting biological particles based upon the collected identification information.

BACKGROUND ART

Recent rapid development of the biotechnology expands a demand of a flow cytometer and a cell sorter which are more commonly used in the various fields of medicine and biology for automatic analysis and fractionation of multiple cells. In general, the flow cytometer forms a stream of a sheath flow containing various cell particles in line, which are collected from a living body (blood, etc.) and dyed with a fluorescent labeling reagent, and emits laser beam onto the stream of the cell particles to detect light excited by and/or scattered at the cell particles (i.e., forward-scattered light, and side-scattered light, and multicolor fluorescence varying based on the fluorescent labeling reagent used) so that each of the cell particles in the stream is analyzed based upon the detected light In general, the flow cytometer converts the detected light having identification information of the cell particles into electrical signals, so as to statistically evaluate electrical signals for a mass of the cells collected from the sample, thereby allowing diagnosis of a health condition such as a disease of the living body. Further, the cell sorter also uses the electrical signals having identification information to selectively charge droplets containing a particular group of the cells to be sorted, and applying a DC electric field across a dropping path of the droplets, thereby selectively retrieving or sorting the desired cells.

Figure 1:
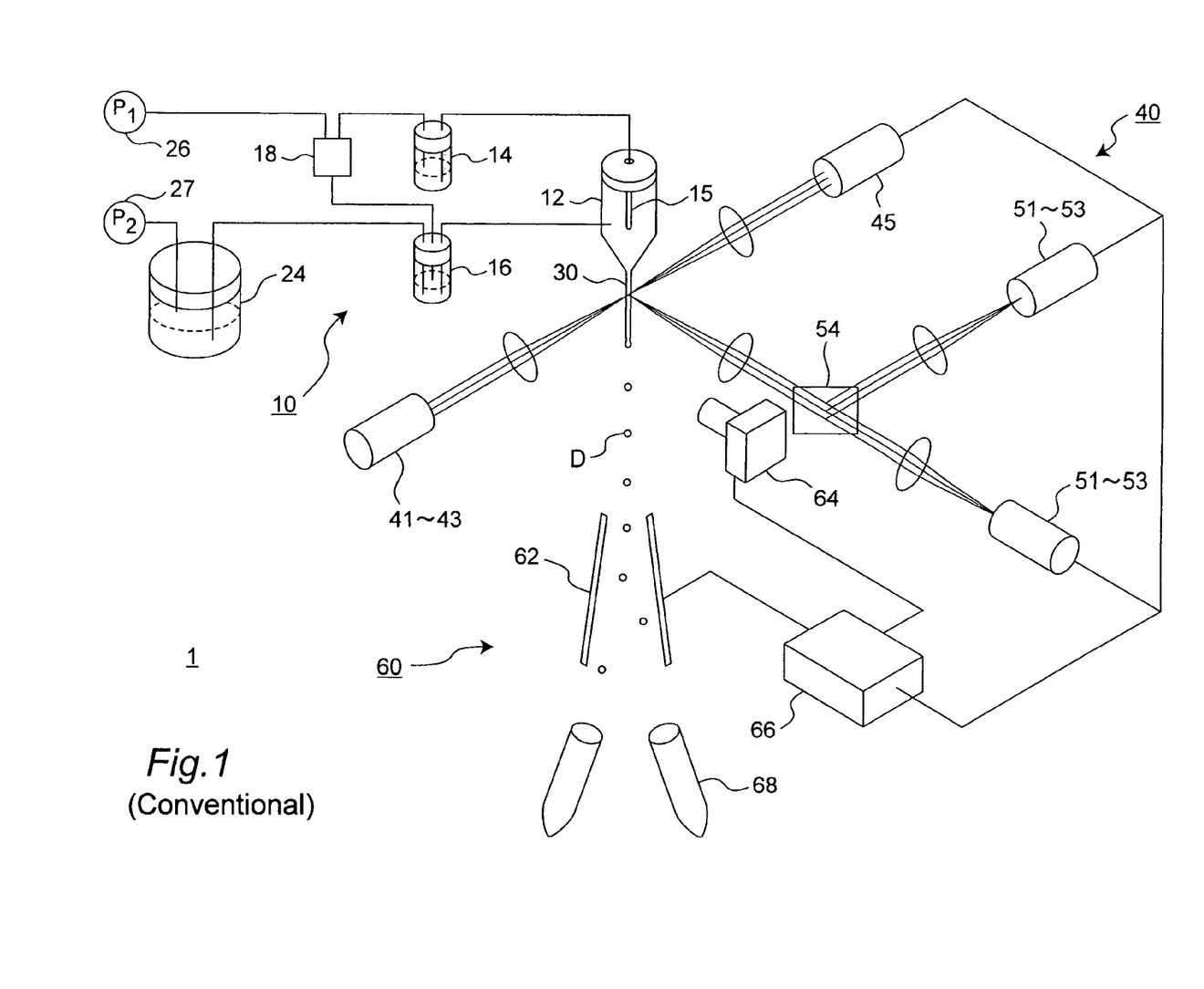
FIG. 1 is a schematic overall view of a cell sorter showing a general structure thereof.

FIG. 1 is a schematic view of the cell sorter 1, illustrating a general framework thereof. In general, the cell sorter 1 includes a fluid flow mechanism 10, an optical mechanism 40, and a sorting mechanism 60. The fluid flow mechanism 10 forms a stream of a sheath flow containing various cell particles, which are collected from a living body and dyed with a fluorescent labeling reagent. The optical mechanism 40 emits laser beams having different wavelengths onto each of the cell particles to detect scattering light and fluorescence. The sorting mechanism 60 analyzes electrical signals obtained from scattering light and fluorescence to sort the cell particles in the sample by providing the droplet containing the desired cell particles with electric charge at a given timing.

More particularly, as shown in FIG. 1, the fluid flow mechanism 10 includes a cylindrical flow chamber 12 defining a sheath flow, a sample container 14 for receiving suspension liquid containing fluorescently-labeled cell or biological particles, and a sheath container 16 for receiving a sheath liquid. Also, the fluid flow mechanism 10 includes a pressure controller 18 for controlling atmospheric pressure within the sample container 14, a plenum container 24 for storing a volume of the sheath liquid and supplying it to the sheath container 16, and air pumps 26, 27 for supplying compressed air to the sample container 14 and a plenum container 24, respectively. Provided downstream (below) the flow chamber 12 is a flow cell 30 having a cross section smaller than the flow chamber 12. In the fluid flow mechanism 10 so structured, upon activation of the air pumps 26, 27, the sample suspension liquid received within the sample container 14 and the sheath liquid received within the sheath container 16 are delivered to the flow chamber 12, to define a cylindrical laminar flow or sheath flow which encompasses the sample suspension liquid with the sheath liquid. Then, the sheath flow is ejected from an orifice on the bottom of the flow-path block 28 as a jet flow, and eventually, a series of discrete droplets D are separated from the jet flow at the break-off point BP when the flow cell 30 is applied with oscillation having a predetermined frequency.

The optical mechanism 40 emits a plurality of excitation laser beams having different wavelengths onto each of the cell particles running one-by-one in a line through the jet flow, and detects the forward- and side-scattered lights scattered at the cells and a variety of fluorescences having different wavelengths excited at the cells to output the identification information thereof to the sorting mechanism 60.

The sorting mechanism 60 identifies a type of each of the cell particles based upon the identification information of the cell particles, and uses an electrode positioned beneath the flow cell 30 to provide the cell particle at the break-off point BP with electric charge of polarity selected in accordance with the identification information, so that the droplets containing the charged cell particles are deflected on the dropping path between a pair of deflectors 62 having a given electrical potential difference, and are sorted into one of targeted slide glasses.

According to Patent Document 1 (Japanese Patent Publication 2005-315799, of which US counterpart is U.S. Pat. No. 7,417,734) commonly assigned to the applicant of the present application, which is incorporated herein by reference into the present application, the cell particles moving through the flow cell 30 are assumed to run along the center of the flow cell 30 at an uniform speed regardless of the cell particles. Thus, the sorting mechanism 60 of Patent Document 1 is designed to charge the cell particle that is assumedly located at the break-off point BP, at a fixed timing irrespective of the moving speed thereof.

DISCLOSURE OF INVENTION

Problems to be Solved by Invention

Figure 2:
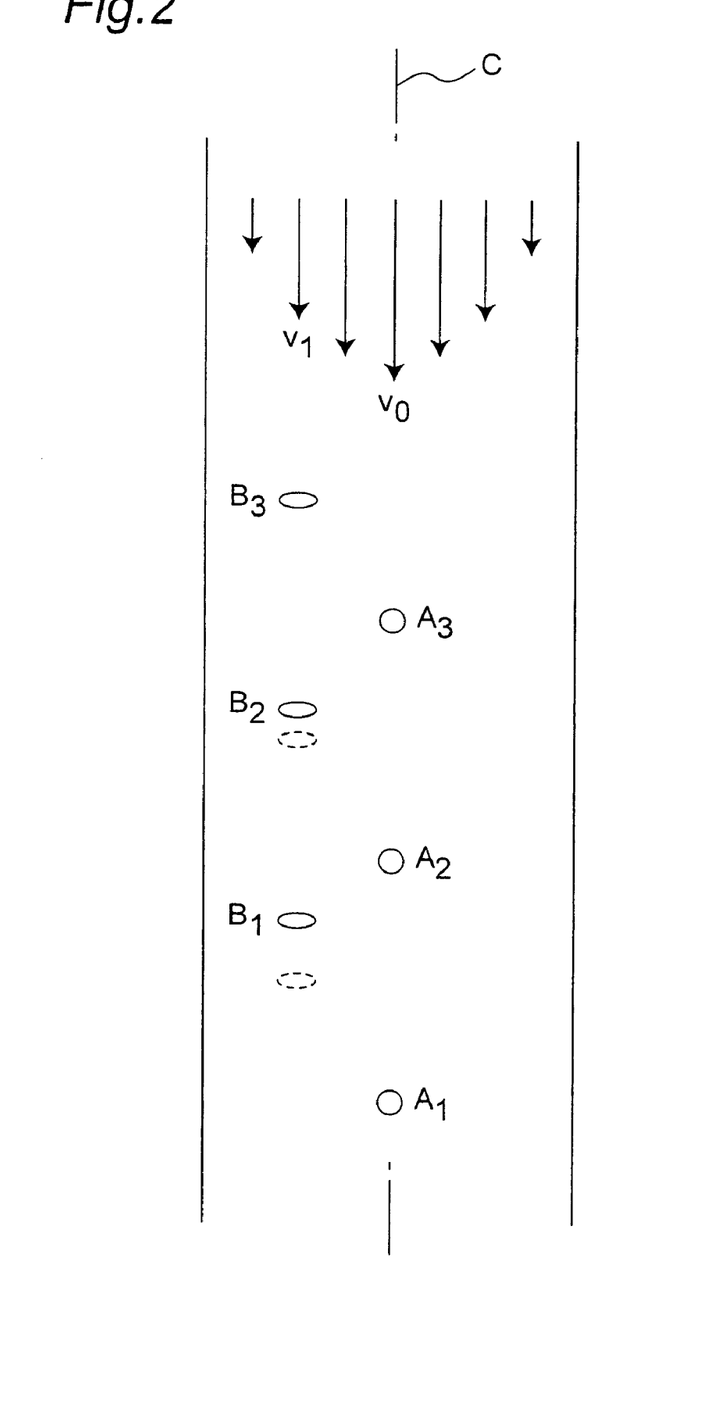
FIG. 2 is an enlarged conceptual view of the sheath flow, showing various cell particles running therethrough, which may have different moving speed.

However, in reality, due to different size and shape of each cell particle, the cell particle moving through the flow cell 30 does not always run along the center C of the flow cell 30, rather moves along an off-axis path deviated away from center C thereof as shown in FIG. 2. It is reported that the cell particle moving through the flow cell 30 has the moving speed which is typically proportional to square of distance from the side wall of the flow cell 30 to the cell particle, that is, the velocity of the cell particle is zero on the side wall, and the maximum value of $V_0$ on the center C of the flow cell 30. FIG. 2 shows, for example, cell particles $A_1, A_2, A_3$, moving along the center C of the flow cell 30 and having the maximum velocity $V_0$, and cell particles $B_1, B_2, B_3$, moving off from the center C of the flow cell 30 and having the velocity $V_1$ slower than the maximum velocity $V_0$, which alternately run through the flow cell 30 ($A_1, B_1, A_2, B_2, A_3, B_3$). Each of the cell particles $B_1, B_2, B_3$ moves, as shown by the solid ellipse lines, delayed behind the positions as shown by the imaginary ellipse lines which were assumed by the Patent Document 1. Thus, the cell particles $B_1, B_2, B_3$ charged at a fixed timing irrespective of its velocity thereof cannot reach to the break-off point BP, and therefore, the droplets containing those cell particles $B_1, B_2, B_3$ cannot be charged properly, reducing the recovery rate of the sorted cell particles within the targeted slide glasses. Also, the delayed cell particle (e.g., $B_1$) and the cell particle (e.g., $A_1$) having the maximum velocity $V_0$ may reach at the break-off point BP and be charged simultaneously. This may eventually form the single droplet having two different types of the cell particles ($A_1$, $B_1$), which mixes undesired cell particles in the sorted cell particles, and therefore, may reduce purity of desired cell particles in the sorted liquid.

One of embodiments according to the present invention is to provide a cell sorter, which calculates a delay time required for each cell particle to reach at the break-off point BP based upon the moving speed thereof, and charges the targeted cell particle at an appropriate timing, thereby to improve the recovery rate thereof and/or to ensure sorting the desired cell particles from undesired ones, thereby increasing the purity of the desired cell particles in the sorted liquid.

Means to Solve the Problems

In particular, the first embodiment of the present invention is to provide a system for sorting biological particles in a liquid flow, such as a cell sorter, which comprises an optical mechanism emitting laser beam onto each of the biological particles to detect light therefrom, a controller determining a moving speed of each of the biological particles in the liquid flow in accordance with the light detected therefrom, and an electric charger charging each of the biological particles based upon the moving speed thereof.

Preferably, the controller may monitor, based upon the moving speed, a position of each of the biological particles within at least one droplet flow separating at a break-off point from the liquid flow, and the controller may control the electric charger to charge each of the biological particles based upon the position thereof.

More preferably, the controller may collect identification information of each of the biological particles based upon the light detected therefrom, and the controller may control the electric charger to charge the biological particles with electricity of polarity selected in accordance with the identification information.

More preferably, when a plurality of the biological particles having identification information different from one another are contained within the at least one droplet flow, the controller may control the electric charger not to charge the biological particles. Alternatively, when a plurality of the biological particles having identification information same as one another are contained within the at least one droplet flow, the controller may control the electric charger to charge the biological particles.

Also, when the moving speed of the biological particle is less than a predetermined threshold, the controller may control the electric charger not to charge the biological particle.

In particular, the optical mechanism may include a first optical source emitting light onto the biological particle at a first position, a first optical detector receiving light from the biological particle emitted by the first optical source, a second optical source emitting light onto the biological particle at a second position, and a second optical detector receiving light from the biological particle emitted by the first optical source. The controller may calculate, in accordance with optical signals of the lights received from the first and second optical detectors, the moving time required for each of the biological particles to move between the first and second positions, so as to determine the moving speed of the biological particle.

Preferably, the system may further comprises a stationary imaging device taking an image of an imaging range covering the liquid flow and the break-off point. The controller may determine a flow distance between the first position and the break-off point, and a droplet-droplet distance between two adjacent droplets separated from the liquid flow, in accordance with the image taken by the stationary imaging device, and the controller may calculate a delay time required for the biological particle to move from the first position to the break-off point, based upon the flow distance, the droplet-droplet distance, and the moving time.

Preferably, the light received from the biological particle, which is emitted by the first and second optical sources, is either one selected from a group of a forward-scattered light and a side-scattered light. More preferably, the lights emitted from the first and second optical sources onto the biological particle are laser beams having wavelength different to each other.

Also, the second embodiment of the present invention is to provide a process for sorting biological particles in a liquid flow, which comprises emitting laser beam onto each of the biological particles to detect light therefrom, determining a moving speed of each of the biological particles in the liquid flow in accordance with the light detected therefrom, and charging each of the biological particles based upon the moving speed thereof.

Further, the third embodiment of the present invention is to provide a system for sorting biological particles in a liquid flow, which may further comprises a sheath container for receiving a sheath liquid, a plenum container for supplying the sheath liquid to the sheath container via an extension tube, a first pressure source connected to the plenum container, a sample container for receiving a sample liquid containing the biological particles, a second pressure source connected to the sheath container, a flow cell in fluid communication with the sheath container and the sample container, defining the liquid flow which encompasses the sample liquid with the sheath liquid, and a sheath temperature controller for controlling temperature of the sheath liquid so as to keep it stable.

Preferably, the sheath temperature controller may include an insulation jacket provided around the extension tube. Also, the sheath temperature controller controls the temperature of the sheath container in a range between 4-42 degrees centigrade.

More preferably, the system may further comprises a sample temperature controller controlling temperature of the sample liquid so as to keep it in a thermal range where the biological particles can survive, and the sheath temperature controller may keep the sheath fluid in the thermal range where the biological particles can survive as well.

Advantages of Invention

The embodiment according to the present invention achieves the cell sorter of which recovery rate and purity of the desired cell particles can be improved.

BRIEF DESCRIPTION OF REFERENCE NUMERALS

1: cell sorter,
10 fluid flow mechanism, 12: cylindrical flow chamber, 14: sample container, 15: sample tube, 16: sheath container, 17: sheath tube, 18: pressure controller, 20: extension tube, 21: insulation jacket or bed (sheath temperature controller), 23: temperature stabilizer, 24: plenum container, 26, 27: air pump, 28: flow-path block (path-defining structure), 30: flow cell, 32: oscillator, 34: orifice, 36 charging electrode (electric charger),
40: optical mechanism, 41: first optical source (blue), 42, second optical source (red), 43: third optical source (ultraviolet), 45: forward-scattered light detecting device, 46: optical detector, 51: first fluorescence/side-scattered light detecting device, 52: second fluorescence/side-scattered light detecting device, 53: third fluorescence/side-scattered light detecting device, 54: half-mirror, 55: band-pass filter,
60: sorter mechanism, 62: deflector, 64: stationary imaging device, 66: controller, 68: slide glass, 70: imaging range or region,
SSC1, SSC2: optical detector, FL-FL8: photomultiplier tube, $A_1$-$A_3$: standard bead, $B_1$-$B_3$: cell particle, BP: break-off point, $F_S$: sheath flow, $F_J$: jet flow, D: droplet, DC: constricted regions, $DF_1$-$DF_5$: droplet flows, TP: targeted cell particle, FP: false cell particle

BEST MODE FOR CARRYING OUT THE INVENTION

Referring to attached drawings, embodiments of a cell sorter according to the present invention will be described herein. In the description, a couple of terms for indicating the directions (for example, "upper" or "lower") are conveniently used just for facilitating clear understandings, it should not be interpreted that those terms limit the scope of the present invention.

A cell sorter 1 illustrated in FIG. 1, in general, includes a fluid flow mechanism 10 forming a stream of various cells dyed with a fluorescent labeling reagent in line within a sheath flow, an optical mechanism 40 emitting multiple laser beams of different wavelengths onto each of the cell particles and detecting various fluorescence and scattering light, and a sorting mechanism 60 analyzing electrical signals obtained from fluorescence and scattering light to sort the cell particles in the sample by charging the cell particles at a given timing.

[1. Fluid Flow Mechanism]

Figure 3:
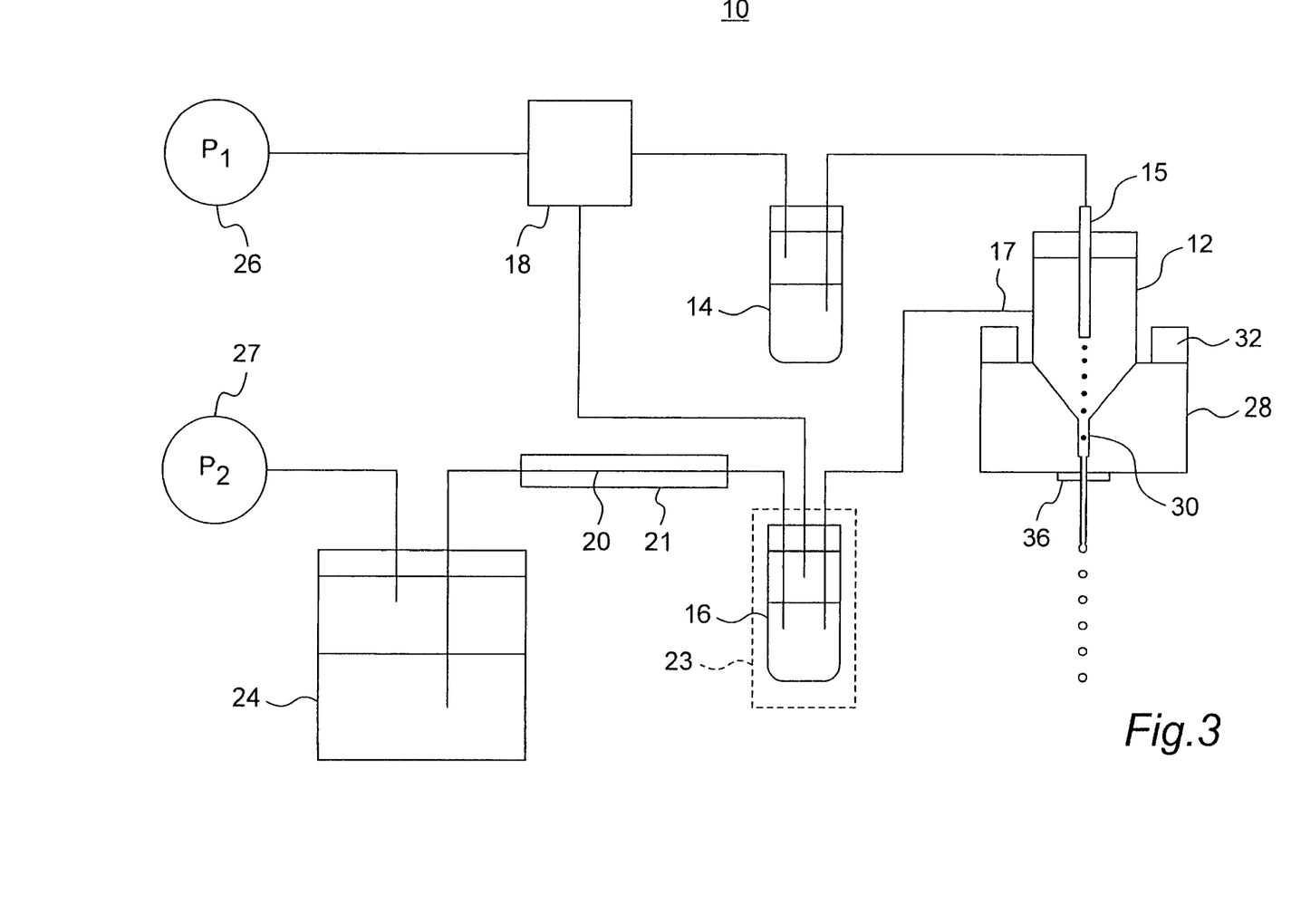
FIG. 3 is a schematic view of the fluid flow mechanism of the embodiment according to the present invention.
Figure 4:
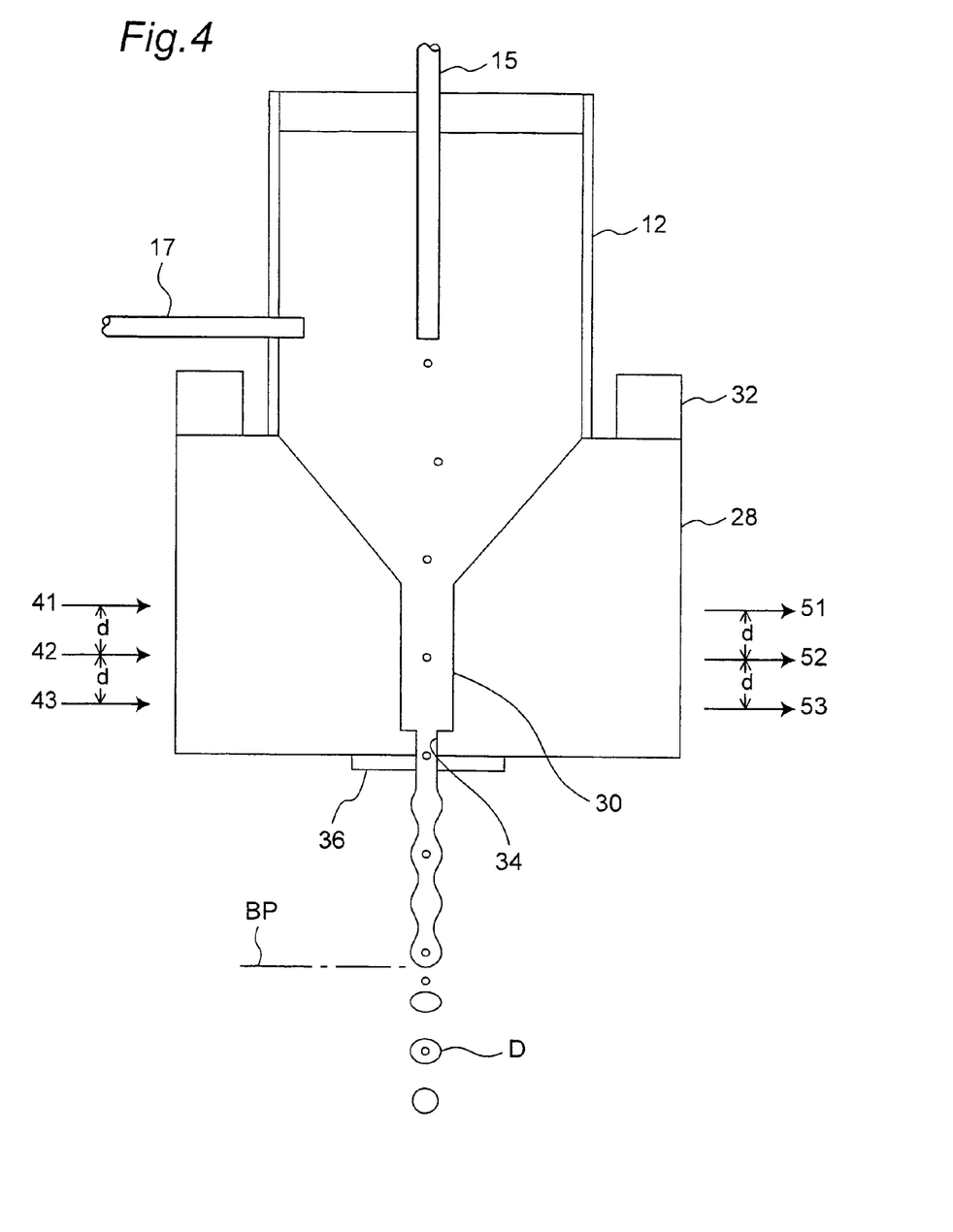
FIG. 4 is an enlarged view showing the flow chamber, the flow cell, and the jet flow of FIG. 3.

With reference to FIGS. 1, 3, 4, the fluid flow mechanism 10 will be described herein. The fluid flow mechanism 10 includes a cylindrical flow chamber 12 for defining a sheath flow. Also, it includes a sample container 14 for receiving sample suspension liquid containing cell particles fluorescently labeled with fluorescent reagents such as fluorescent pigment and a fluorescent-labeled monoclonal antibody, and a sheath container 16 for receiving a sheath liquid. The sample suspension liquid is supplied to a flow chamber 12 from a sample tube 15 aligned along the central axis of the flow chamber 12, while the sheath liquid is supplied to the flow chamber 12 through a sheath tube 17 connected to a peripheral port thereof.

Further, as illustrated in FIG. 3, the fluid flow mechanism 10 includes a pressure controller 18 for controlling atmospheric pressure within the sample container 14, and an air pump 26 for supplying compressed air to the pressure controller 18. Also, it includes a plenum container 24 for storing a volume of the sheath liquid and supplying it to the sheath container 16 via an extension tube 20 having a substantial length, and another air pump 27 for supplying compressed air to the plenum container 24. Preferably, the pressure controller 18 may monitor the pressure within the sheath container 16 and controls it so as to be higher than that within the sample container 14 by a predetermined pressure gap.

The flow cytometer and the cell sorter according to the present invention uses an image processing technology as described below to measure a length of the jet flow and a distance between the adjacent droplets in the captured image, thereby to determine the timing for charging the cell particles (delay time). In order to achieve fine sorting of the cell particles, it is required to stabilize the length of the jet flow and the distance between the adjacent droplets. However, it is known that the jet flow length and the droplet-droplet distance may be influenced based on the temperature of the sheath liquid. Thus, the higher temperature of the sheath liquid causes the less viscosity thereof, the longer jet flow length, and the longer droplet-droplet distance. Reversely, the lower temperature of the sheath liquid causes the greater viscosity thereof, the shorter jet flow length, and the shorter droplet-droplet distance.

According to the present embodiment, the fluid flow mechanism 10 includes means (a sheath temperature controller) for stably maintaining the temperature of the sheath liquid supplied from the plenum container 24. In particular, while the sheath liquid is delivered from the plenum container 24 through the extension tube 20 to the sheath container 16, the temperature thereof may be influenced by and varied closer to the room temperature. Therefore, it is preferable to provide an insulation jacket or bed (sheath temperature controller) 21 around the extension tube 20, thereby to minimize the influence of the room temperature. Also, a temperature stabilizer 23 as shown with a imaginary box may be provided for housing the sheath container 16, to keep the temperature of the sheath liquid as being stable. Although not limited thereto, the temperature of the sheath liquid may be controlled in a range between 4-42 degrees centigrade. This stably maintains the temperature (and the viscosity) of the sheath liquid, thereby to control the jet flow length and the droplet-droplet distance so that the recovery rate in sorting and the purity of the sorted cell particles are stable.

Similarly, even where the cell particles in the sample suspension liquid within the sample container 14 are susceptive to the temperature and survives only in a limited temperature range, the fluid flow mechanism 10 of the present embodiment advantageously includes means (a sample temperature controller, not shown) for stably maintaining the temperature of the sample suspension liquid within the sample container 14 as well. Such a sample temperature controller may be structured similar to that of the sheath temperature controller. Alternatively, a single chamber (not shown) may be provided for housing both of the sample container 14 and the sheath container 16 to control the temperature of the sample suspension liquid and the sheath liquid.

Furthermore, as illustrated in FIG. 4, provided beneath the flow chamber 12 is a funnel-shaped flow-path block 28 (path-defining structure) made of transparent material such as quartz, glass, fused silica, and transparent plastic, etc. Downstream the funnel-shaped structure, the flow-path block 28 also defines a flow cell 30 having a reduced cross section. Also, provided on the upper circumference of the flow-path block 28 is an oscillator 32 using a frequency-variable piezoelectric element (e.g., the frequency may be 60 kHz). In addition, provided on the bottom surface of the flow-path block 28 are an orifice 34 and a charging electrode or charger 36 in contact with the sheath flow for providing the cell particles in the sheath flow with electric charge of polarity switched in accordance with the cell particles.

In the fluid flow mechanism 10 so structured, the suspension liquid received within the sample container 14 and the sheath liquid received within the sheath container 16 are supplied into the flow chamber 12, upon activation of the air pumps 26, 27, thereby to define a cylindrical laminar flow or sheath flow which encompasses suspension liquid with the sheath liquid. Then, the sheath flow is ejected from the orifice 34 of the flow-path block 28 as a jet flow, and along with oscillation of the flow-path block 28 by the oscillator 32 at a predetermined frequency, a horizontal cross section of the jet flow is modulated along the vertical direction in synchronization with the predetermined frequency of the oscillator 32 so that a series of discrete droplets D are separated from the jet flow at the break-off point BP, as illustrated in FIG. 4.

As will be described herein in detail, at the assumed timing when the cell particle to be sorted reaches at or just before the break-off point BP, the sheath flow is charged by the charging electrode 36 with the polarity selected in accordance with the identification information of the cell particle so as to form the charged droplet D with the cell particle. A sorter mechanism 60 of FIG. 1 further includes a pair of deflectors 62 provided beneath the charging electrode 36, having a given electrical potential difference therebetween, for sorting the charged droplet D with the cell particle falling between the deflectors 62, into the slide glasses 68. Although not described herein in detail about a process how to collect the identification information of the cell particle to be sorted, the process disclosed in the aforementioned Patent Document 1 for example, may be applied to the present invention, which is incorporated by reference into the present application.

[2. Optical Mechanism]

Next, referring to FIGS. 1-5, the optical mechanism 40 will be described herein.

Figure 5:
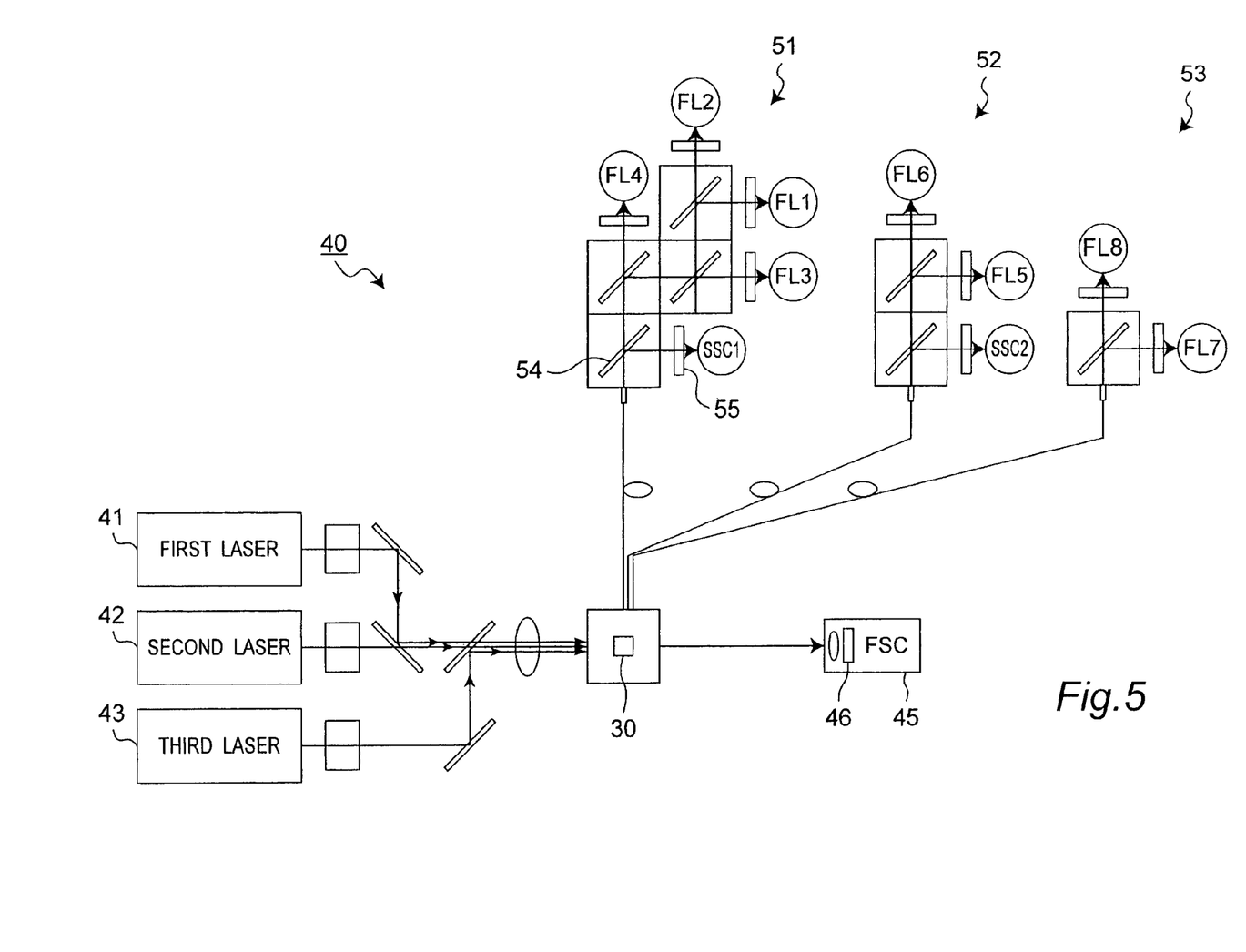
FIG. 5 is a schematic view of the optical mechanism of the embodiment according to the present invention.

The optical mechanism 40 includes first, second, third optical sources 41, 42, 43 for sequentially emitting laser beams of different wavelengths on each of the cell particles moving in line through the flow cell 30. It also includes a forward-scattered light detecting device 45 for detecting the forward-scattered light scattered at the cell particle by means of the first optical source 41, and first, second, third fluorescence/side-scattered light detecting devices 51, 52, 53 for detecting fluorescence and forward-scattered lights with laser beams from the first, second, third optical sources 41, 42, 43, respectively.

In particular, the first, second, third optical sources 41, 42, 43 preferably emit light such as coherent laser beams. For example, the first optical source 41 may be a DPSS laser (Diode Pumped Solid State Laser) emitting, e.g., a blue laser beam (peak wavelength: 488 nm, output: 20 mW). The second optical source 42 may be a diode laser emitting, e.g., a red laser beam (peak wavelength: 635 nm, output: 20 mW), and the third optical source 43 may be a diode laser emitting, e.g., a near ultra-violet laser beam (peak wavelength: 375 nm, output: 8 mW).

In FIG. 5, the forward-scattered light detecting device 45 has a photodetector 46 for detecting only the blue forward-scattered light (FSC), which is scattered at the cell particle and transmitted through a band-pass filter allowing selective transmission of the blue laser beam.

Also, the first, second, third fluorescence/side-scattered light detecting devices 51, 52, 53 are structured to detect the side-scattered light scattered at the cell particle and the fluorescence excited by red, blue, and ultraviolet laser beams. It should be noted that detection of the side-scattered light by the third optical source 43 is not essential in the present embodiment, the third light detecting device 43 is shown in FIG. 5 as detecting only the fluorescence.

More particularly, in FIG. 5, the first (blue) fluorescence/side-scattered light detecting device 51 is illustrated to include an optical detector SSC1 for detecting the scattered light from the cell particle with the blue laser beam, and a plurality of photomultiplier tubes FL1-FL4 for electrically amplifying and detecting faint fluorescence. The second (red) fluorescence/side-scattered light detecting device 52 is also illustrated to have another optical detector SSC2 for detecting the scattered light and photomultiplier tubes FL5-FL6 for detecting fluorescence from the cell particle with the red laser beam, and the third (ultra-violet) fluorescence detecting device 53 is shown as having only photomultiplier tubes FL7-FL8 for detecting fluorescence from the cell particle with the ultra-violet laser beam. Further each of the fluorescence/side-scattered light detecting devices 51, 52, 53 includes a plurality of half-mirrors 54 and a plurality of band-pass filters 55.

The first, second, third optical sources 41, 42, 43 are arranged at fixed positions relative to the flow cell 30 so that each of the laser beams are radiated onto the flow cell 30 at points aligned along the sheath flow direction (vertical direction) where each of adjacent two points has the same distance or gap (d). Similarly, the first, second, third fluorescence/side-scattered light detecting devices 51, 52, 53 are arranged to receive the fluorescence/side-scattered light from the flow cell 30 at points aligned along the vertical direction with the same gap (d). Therefore, when it is determined that a certain time ($t_0$) has passed after detecting the fluorescence/side-scattered light at the first point of the flow cell 30 by the first light detecting devices 51 before detecting the fluorescence/side-scattered light at the second point by the second light detecting devices 52, the moving speed ($v_0$) of the cell particle running within the sheath flow is represented as following equation:

$$v_0 = d/t_0 \tag{1}$$

Thus, a controller 66 of the sorter mechanism 60 can calculate the moving speed ($v_0$) of the cell particle moving within the sheath flow by measuring the time ($t_0$) between detection of the blue side-scattered light by the optical detector SSC1 and detection of the red side-scattered light by the optical detector SSC2, as will be later described in detail, and by substituting it into the aforementioned equation (1). Also, since the fluorescence detected by the photomultiplier tubes FL1-FL8 have wavelength spectrum special or unique to the cell particle, the controller 66 can collect identification information of the cell particle by analyzing the wavelength spectrum of the fluorescence, so as to determine or identify the type of each of the cell particles.

Although in the foregoing description, the side-scattered light is used for measuring the moving speed ($v_0$) of the cell particle, the front-scattered light may also be used as well. Thus, the forward-scattered light detecting device 45 may be provided with a blue band-pass filter and a red band-pass filter for selectively transmitting blue laser beam and red laser beam, respectively, so that the moving speed ($v_0$) may be calculated by the aforementioned equation (1) with the measured time ($t_0$) between detection of the forward-scattered light of the blue laser beam and red laser beam.

[3. Sorting Mechanism]

Next, referring to FIGS. 1-6, the sorting mechanism 60 will be described herein. As illustrated in FIG. 1, the sorting mechanism 60 includes a pair of deflectors 62 having a given electrical potential difference, a stationary imaging device 64, and a controller 66 which is connected with the deflectors 62, stationary imaging device 64, and the fluorescence/side-scattered light detecting devices 51, 52, 53 (the optical detectors SSC1, SSC2 and the photomultiplier tubes FL1-FL8).

Figure 6:
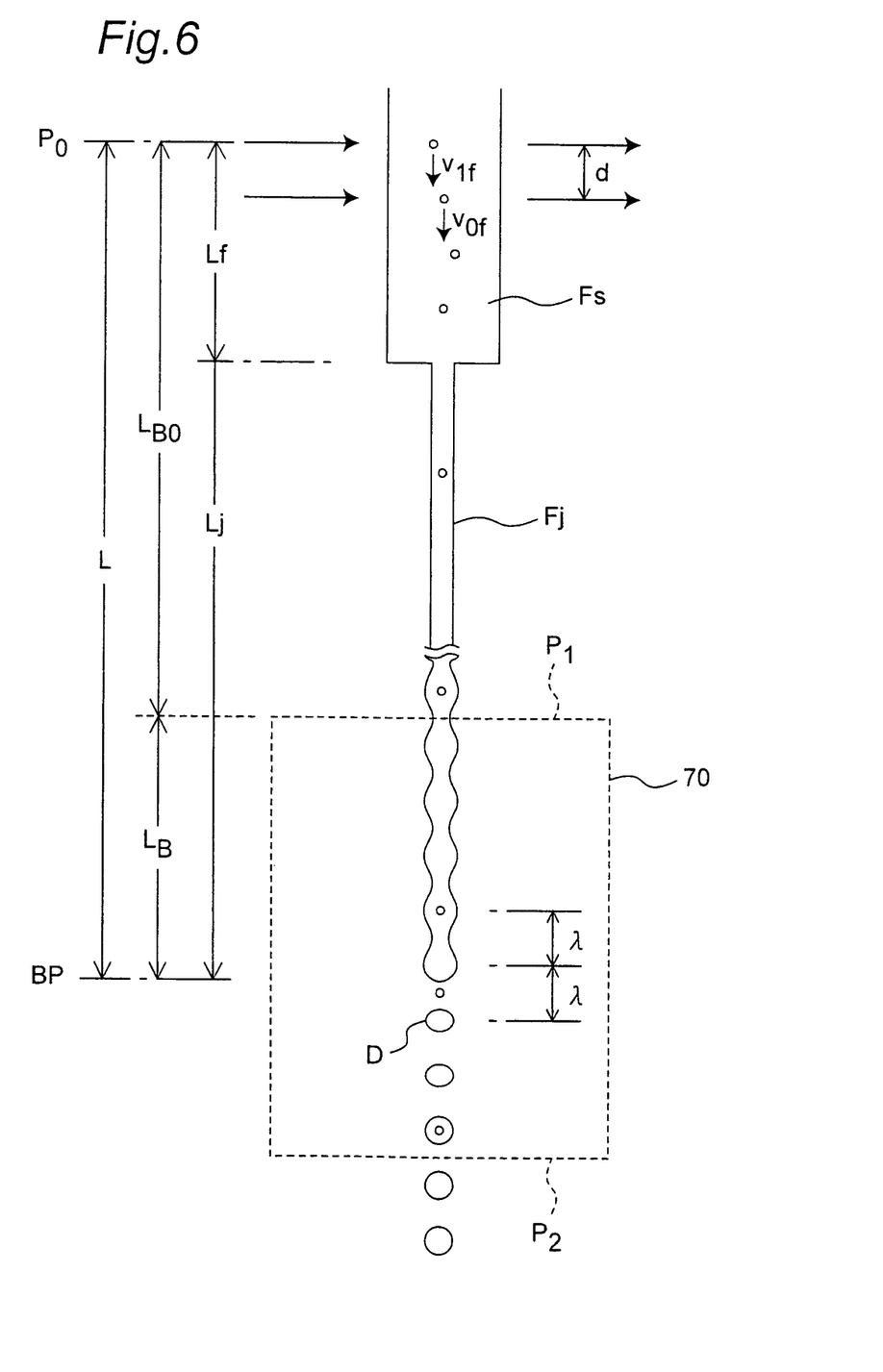
FIG. 6 is an enlarged view showing the sheath flow, the jet flow, and the droplets separated therefrom at the break-off point.

FIG. 6 is a schematic view showing the sheath flow $F_S$ in the flow cell 30, the jet flow $F_J$ ejecting from the orifice of the flow cell 30, and a series of the droplets D separated at the break-off point BP from the jet flow $F_J$. As briefly discussed above, when the flow-path block 28 is oscillated by the oscillator 32 provided thereon at a predetermined frequency (for example, f=60 kHz), a horizontal cross section of the jet flow $F_J$ is modulated (varied) along the vertical direction in synchronization with the predetermined frequency of the oscillator 32 as shown in FIG. 6. It should be noted that the modulation period (λ), which is the distance between the adjacent local maximum points or local minimum points and also the gap between the adjacent droplets D, is kept constant.

The stationary imaging device 64, which includes an imaging element such as CCD camera and a stroboscopic lamp (both not shown), is fixedly arranged at a stationary position relative to the flow cell 30 so as to take an image of the jet flow $F_J$ and the droplets D close to the break-off point BP in a fixed imaging range defined by a dotted rectangle of FIG. 6, which is partially defined between the imaging positions $P_1$, $P_2$ upstream and downstream from the break-off point BP. Meanwhile, the stroboscopic lamp is designed to intermittently flicker onto the jet flow $F_J$ and the droplets D in the imaging range at the same frequency (f) as the oscillator 32. Thus, the stationary imaging device 64 takes the image of the jet flow $F_J$ and the droplets D at the same frequency (f), which seems like motionless as illustrated in FIG. 6.

Since the stationary imaging device 64 is fixedly positioned relative to the flow cell 30, the distance ($L_{B0}$) between the position $P_0$ where the first (blue) light detecting device 51 receives the blue side-scattered light scattered at the cell particle and the position $P_1$ of the fixed imaging range 70 can be kept constant. According to the invention of Patent Document 1, the stationary imaging device 64 continues to monitor the modulation period (λ), and the accurate distance ($L=L_{B0}+L_B$) between the position $P_0$ and the break-off point BP is calculated in real time by determining the distance ($L_B$) with an image processing technique, so that the accurate distance (L) is used for correcting the delay time when the cell particle at the break-off point BP is charged by the charging electrode 36. Yet, Patent Document 1 assumes that every cell particle has the identical speed irrespectively to size and/or shape of the cell particle.

However, in reality, the cell particle does not always move along the center of the flow cell 30 due to variation of size and/or shape of the cell particle. Rather, some of the cell particles may run off the center of the flow cell 30, which in turn reduces the speed of the cell particles relative to ones running along the center. Those slower cell particles need more time to reach to the break-off point BP than the center-running cell particles, which eventually causes failure to promptly charge the slower cell particles at the break-off point BP and/or causes contamination of the undesired cell particles within the cell particles to be sorted and collected.

To address this drawback, the embodiment of the present invention determines the moving speed of each of the cell particles based upon the moving time ($t_0$) which is required to move a given gap between the detection points by the optical detectors SSC1, SSC2, and precisely calculates the corrected delay time for each cell particle to reach to the break-off point BP based upon the moving speed thereof, thereby to promptly charge each cell particle in accordance with the corrected delay time.

Again referring to FIGS. 1-6, a detailed discussion will be made herein with regard to a process for calculating the corrected delay time for each cell particle to reach to the break-off point BP based upon the distance (L) between the position $P_0$ and the break-off point BP, as well as the modulation period (λ) of the jet flow $F_J$ (or the droplet-droplet gap between the adjacent droplets D), which is measured by means of the image processing technique.

[Step 1] (Pre-Measurement of $L_{B0}$ with Standard Beads)

Although the stationary imaging device 64 is fixedly arranged at a stationary position relative to the flow cell 30 so that the distance (L) between the position $P_0$ and the break-off point BP is constant as described above, the stationary imaging device 64 may be aligned less perfectly to the fluid flow mechanism 10 due to tolerance in assembling thereof. Consequently, following steps is to be taken to precisely measure the distance ($L_{B0}$) between the position $P_0$ and the imaging position $P_1$ of the imaging range, after assembling the stationary imaging device 64 with the fluid flow mechanism 10 and before actual sorting of the cell particles in the sample suspension liquid.

A sample suspension liquid is prepared, containing a plurality of standard beads, each of which is known to have substantially spherical shape of uniform and small size and move substantially along the center of the flow cell 30. Then, a preliminary sorting is performed with this sample suspension liquid. In this preliminary sorting, the standard beads are introduced into the flow cell 30 with a substantial gap to each other. At an appropriate time (T) after the first optical detector SSC1 detects the standard bead, the charging electrode 36 is energized to provide the standard bead with electricity of a predetermined polarity, so that the charged droplet with the standard bead is sorted into the slide glass 68 by the pair of the deflectors 62 when dropping therebetween. When the time (T) changes, the amount of the standard beads in the droplets D collected in the slide glass 68 is also varied, in which a Gaussian distribution of amount of the collected standard beads in the slide glass 68 can be plotted over the time (T), which has the peak value ($T_0$). This peak value ($T_0$) is equivalent to the delay time that is required for each standard bead to move from the position $P_0$ to the break-off point BP. Thus, the controller 66 can precisely determine the delay time ($T_0$) of the standard bead.

The standard bead has the moving speed ($v_{0f}$) in the flow cell 30 and the moving speed ($v_{0j}$) in the jet flow $F_J$. The moving speeds ($v_{0f}$, $v_{0j}$) have a relationship which can be expressed with the cross section ($S_f$) of the flow cell 30 and the cross section ($S_j$) of the jet flow $F_J$, as follows.

$$v_{0j} = k * v_{0f}, \quad k = S_f/S_j (>1) \qquad (2)$$

For example, the cross section ($S_f$) of the flow cell 30 and the cross section ($S_j$) of the jet flow $F_J$ are about 20,000 μm and about 3,850 μm, respectively.

As the delay time ($T_0$) for the standard bead to move from the position $P_0$ to the break-off point BP is the total time, i.e., the time to move in the flow cell 30 plus the time to move in the jet flow $F_J$, and therefore, following equation is obtained (FIG. 6).

$$\begin{aligned} T_0 &= L_f/v_{0f} + L_j/v_{0j} \\ &= (k * L_f + L_j)/v_{0j} \end{aligned} \qquad (3)$$

On the other hand, as the image of the jet flow $F_J$ and the droplets D, which is illuminated intermittently at the frequency (f) same as the oscillator 32, seems like motionless as illustrated in FIG. 6, each of the local maximum points (or the local minimum points) of the jet flow $F_J$ and each droplet D move or shift by the distance corresponding to the modulation period ($\lambda$) for the flicker time ($\tau$) corresponding to inverse of the oscillation frequency (f) of the oscillator 32, and the relationship among the moving speed ($v_{0j}$), the flicker time ($\tau$), and the modulation period ($\lambda$) can be expressed as follows.

$$v_{0j} = \lambda/\tau \tag{4}$$

Following equation is obtained by combining the aforementioned equations (3) and (4).

$$T_0/\tau = (k*L_f + L_j)/\lambda \tag{5}$$

The left-hand side of equation (5) is a value of the delay time ($T_0$) divided by the flicker time ($\tau$), which is relevant to the number of the standard beads included in the sheath flow $F_S$ and the jet flow $F_J$ between the position $P_0$ and the break-off point BP. This value ($T_0/\tau$) is referred to as a "drop-delay ($DD_0$)" herein.

$$DD_0 = T_0/\tau = (k*L_f + L_j)/\lambda \tag{6}$$
$$= (L_B + L_{B0})/\lambda$$

Also, equation (5) is modified as follows.

$$L_j = \lambda*T_0/\tau - k*L_f \tag{7}$$

The stationary imaging device 64 is fixedly arranged at a stationary position relative to the flow cell 30 so as to take an image of the jet flow $F_J$ and the droplets D covered by the imaging range or region 70 defined between the image positions P1, P2 indicated by a dotted lines. Also, arranged on the background of the imaging region 70 is an appropriate scale or measurement reference (not shown). Thus, the controller 66 may use the scale and the image processing technique as disclosed in the above-said Patent Document 1 to measure the modulation period ($\lambda$) of the jet flow $F_J$ (or the gap between the adjacent droplets D), and the distance ($L_B$) between the image position $P_1$ and the break-off point BP.

The distance ($L_f$) and the coefficient (k) are unique to the flow cell 30, the flicker time ($\tau$) is known and adjustable, and the delay time ($T_0$) and the modulation period ($\lambda$) can be measured so that the controller 66 uniquely determine the drop-delay ($DD_0$) by precisely calculating the distance ($L_j$) with the aforementioned equation (7) and assigning it to the aforementioned equation (6). Also, as clear in FIG. 6, the distance ($L_{B0}$=L−$L_B$) between the position $P_0$ and the imaging position $P_1$ can be determined. The controller 66 stores in its memory (not shown), the calculated distance ($L_{B0}$) and the drop-delay ($DD_0$) as well as the moving time ($t_0$).

[Step 2] (Measurement for Cell Particles in Sample Suspension Liquid)

When the cell particles in the sample suspension liquid move along the path off the center of the flow cell 30 like the cell particles $B_1$, $B_2$, $B_3$, those cell particles have the moving speed ($v_1$) which is slower than that of the standard bead ($v_0$). In particular, those cell particles have the moving speed ($v_{1f}$) in the flow cell 30 and moving speed ($v_{1j}$) in the jet flow $F_J$. Following equations can be obtained for the cell particle, similar to the aforementioned equations (2) and (3).

$$v_{1j} = k*v_{1f}, \quad k = S_f/S_j(>1) \tag{8}$$

$$T_1 = L_f/v_{1f} + L_j/v_{1j} \tag{9}$$
$$= (k*L_f + L_j)/v_{1j}$$

Following equation is obtained by combining the aforementioned equations (8) and (9).

$$T_1/\tau = (k*L_f + L_j)/\lambda \tag{10}$$

Also, the drop-delay ($DD_1$) is defined as follows.

$$DD_1 = T_1/\tau \tag{11}$$

As mentioned above, when the standard bead having the moving speed ($v_{0f}$) takes the moving time ($t_0$) to move the distance (d) between the detection points of the first and second optical detectors SSC1, SSC2, the moving speed ($v_{0f}$) can be expressed as follows.

$$v_{0f} = d/t_0 \tag{12}$$

Similarly, the cell particle having the moving speed ($v_{1f}$) takes the moving time ($t_1$) to move the distance (d) between the detection points of the first and second optical detectors SSC1, SSC2, the moving speed ($v_{1f}$) can be expressed as follows.

$$v_{1f} = d/t_1 \tag{13}$$

Then, following equation is obtained by combining the aforementioned equations (12) and (13).

$$v_{1f} = (t_0/t_1)*v_{0f} \tag{14}$$

Similarly, following equation is obtained by combining the aforementioned equations (2) and (8).

$$v_{1j} = (t_0/t_1)*v_{0j} \tag{15}$$
$$= (t_0/t_1)*\lambda/\tau$$
$$(\because v_{0j} = \tau/\lambda, \text{ equation (4)})$$

This is assigned to equation (9) to obtain following equation.

$$T_1 = (k*L_f + L_j)*(t_0/t_1)*(\tau/\lambda), \tag{16}$$

Therefore, the drop-delay ($DD_1 = T_1/\tau$) can be obtained as follows.

$$DD_1 = (k*L_f + L_j)/(t_0/t_1)/\lambda \tag{17}$$
$$= DD_0/(t_0/t_1)$$
$$(\because DD_0 = T_0/\tau = (k*L_f + L_j)/\lambda, \text{ equation (6)})$$

In equations (16) and (17), the distance ($L_f$) and the coefficient (k) are unique to the flow cell 30, and the distance ($L_{B0}$) is measured by the above step 1. Also, as the distance ($L_B$) can be measured by means of the stationary imaging device 64 and the image processing technique, the distance ($L_j$=$L_{B0}$+ $L_B$−k*L) can be determined. Further, the flicker time ($\tau$) is known and adjustable, and the moving time ($t_1$, $t_0$) can be measured as well. Therefore, the controller 66 can precisely determine the drop-delay ($DD_1$) and the delay time ($T_1$) for each of the cell particles.

Next, referring to FIGS. 7A-7C, description will be made herein regarding a process (a sorting logic) for applying to the droplet D containing the cell particle, an electric charge of polarity switched in accordance with the identification information of each of the cell particles, at an appropriate timing calculated based upon the drop-delay ($DD_1$) and the delay time ($T_1$).

As defined above, the delay time is the time for the cell particle to move from the position $P_0$ to the break-off point BP, and therefore, once the precise or corrected delay time is calculated for each of the cell particles, the positions or distribution of the cell particles in the jet flow $F_J$ especially close to the break-off point BP can be located or followed at any time. As an example, FIGS. 7A-7C are enlarged views showing the jet flow $F_J$ close to the break-off point BP, in which the jet flow $F_J$ has a horizontal cross section that is modulated at the modulation period ($\lambda$) so as to have a plurality of constricted regions DC having a smaller cross section. Thus, a tip portion of the jet flow $F_J$, which is located close to the break-off point BP between the constricted regions, is separated so as to form an individual droplet D. In the present application, some of portions of the jet flow $F_J$ between the two adjacent constricted regions are defined as "droplet flows DF" hereinafter (five of droplet flows $DF_1$-$DF_5$ are illustrated in FIGS. 7A-7C). In other words, as closer to the break-off point BP, the jet flow (liquid flow) $F_J$ forms the droplet flows DF so that the tip portion thereof closest to the break-off point BP forms the droplet D isolated from the jet flow $F_J$.

Figure 7A:
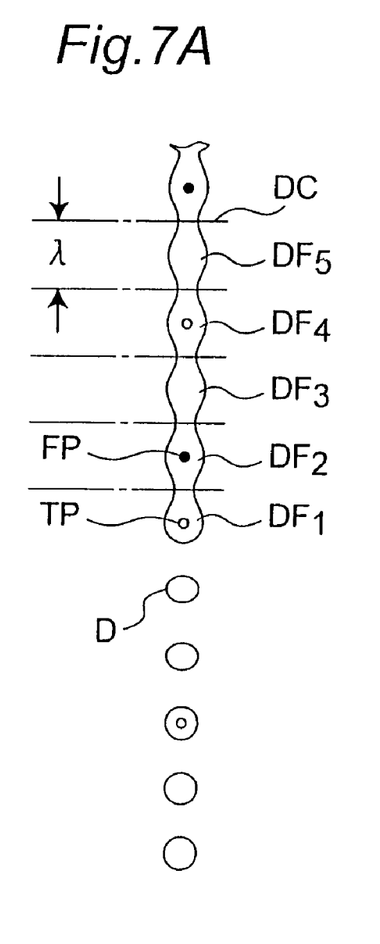
FIGS. 7(a)-7(c) are an enlarged views showing the jet flow and the droplets separated therefrom at the break-off point.

When a desired cell particle to be sorted (referred to as a "targeted cell particle TP") is determined from the delay time as being encompassed within the tip droplet flow $DF_1$ as shown in FIG. 7A by a white small circle, the targeted cell particle TP can reliably be charged by applying voltage onto whole of the jet flow $F_J$ through the charging electrode 36. In other words, the controller 66 according to the embodiment of the present invention continues to follow (monitor) the positions of each of the targeted cell particles TP in the droplet flow $DF_1$ based upon the moving speed (or the delay time) thereof, and promptly charges the targeted cell particle TP through the charging electrode 36 during a given time period (i.e., the modulation period ($\lambda$)) when it is determined as being within the droplet flow $DF_1$ at a given appropriate position.

Figure 7B:
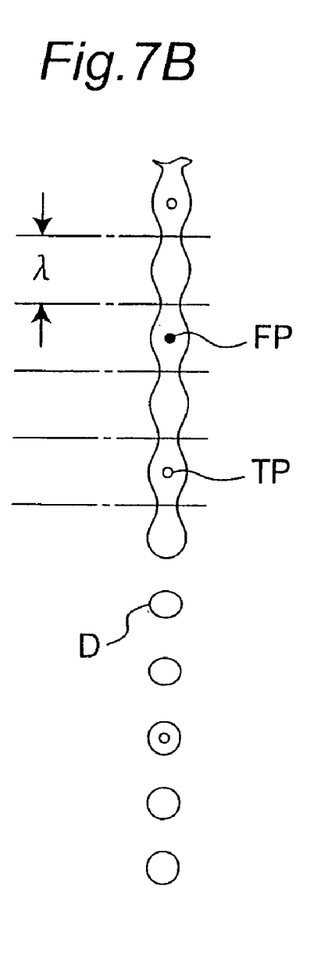
Figure 7C:
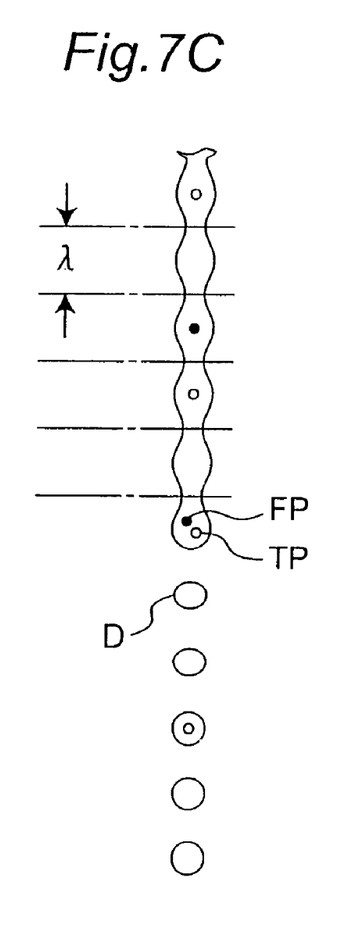

Alternatively, when the targeted cell particle TP is determined as being within a couple of the droplet flows DF (e.g., $DF_2$) as shown in FIG. 7B, the whole jet flow $F_J$ may be charged during double or treble time of the modulation period ($\lambda$), thereby applying electric charge to the targeted cell particle TP. The controller 66 is designed to select the polarity of the charge to the targeted cell particle TP, in accordance with the identification information thereof.

Meanwhile, since the cell particles have the delay time (required to reach to the break-off point BP), which may be different from one another, the targeted cell particle TP and also an undesired cell particle (referred to as a "false cell particle FP", and shown in FIG. 7C by a black small circle) may be determined as being encompassed within the same tip droplet flow $DF_1$. In this situation, in order to improve purity of the sorted or targeted cell particle TP to be collected, the controller 66 according to the embodiment of the present invention may preferably control the charging electrode 36 not to charge the cell particles TP, FP within the droplet flow $DF_1$, which causes failure to collect the droplet D containing both of the targeted and false cell particles TP, FP into the slide glass 68. Alternatively, in order to increase the amount of the targeted cell particles TP with trading the purity thereof, the controller 66 may control the charging electrode 36 to charge the cell particles TP, FP within the droplet flow $DF_1$. Thus, the controller 66 is preferably structured so that a user can choose more purity or more amount of the targeted cell particles TP. Further, as discussed above with reference to FIG. 7B, when the targeted cell particle TP is determined as being within the droplet flows $DF_1$-$DF_3$ close to the break-off point BP, the jet flow $F_J$ may be charged during double or treble time of the modulation period ($\lambda$), for charging the droplet flows $DF_1$-$DF_3$ with the targeted cell particle TP. In addition, due to variation of the delay time for each of the cell particles, the droplet flow $DF_1$ may also contain a plurality of the targeted cell particles, in which the controller 66 preferably controls the charging electrode 36 to charge the droplet flow $DF_1$ with the targeted cell particles TP.

Another exemplary approach for improving purity of the targeted cell particles TP will be described herein. Only in case where the targeted cell particle TP is determined as being in the droplet flow $DF_2$ close to the break-off point BP and no false cell particle FP in the adjacent (upstream and downstream) droplet flows $DF_1$ and $DF_3$, as shown in FIG. 7B, the controller 66 may control the charging electrode 36 to charge only the droplet flow $DF_2$ with the targeted cell particles TP. This eliminates possible contamination of the false cell particle FP within the droplet flow DF containing the targeted cell particle TP due to unexpected reason. Also, although not illustrated in detail, only if the targeted cell particle TP is determined as being within one of the droplet flows $DF_2$-$DF_4$ and no false cell particle FP in the adjacent (upstream and downstream) droplet flows $DF_1$ and $DF_5$, the controller 66 may control the charging electrode 36 to charge the droplet flows $DF_2$-$DF_4$ with the targeted cell particles TP for treble time of the modulation period ($\lambda$). This removes the false cell particle FP securely and reliably thereby to improve impurity of the targeted cell particles TP.

Furthermore, in case where the controller 66 determines the moving speed ($v_{1f}$) in the flow cell 30 calculated by the aforementioned equation (14) as being greater than a predetermined threshold value ($v_{th}$) (i.e., $v_{1f} > v_{th}$), or the delay time ($T_1$) as being greater than a predetermined threshold value ($T_{th}$) (i.e., $T_1 < T_{th}$), the controller 66 may control the charging electrode 36 not to charge the cell particle.

It should be noted that the sorting logic is not limited to the above, and any other approaches may be applied. According to the embodiment of the present invention, the delay time is precisely calculated for each of the cell particles and the position thereof in the droplet flow DF close to the break-off point BP is exactly monitored, so that each of the targeted cell particles is reliably sorted in accordance with the identification information thereof.

More specifically speaking, the position of each of the cell particles in the droplet flow DF close to the break-off point BP can be monitored by the time lag between detections of the cell particle by the first and second fluorescence/side-scattered light detecting devices 51, 52. As discussed with reference to FIG. 2, the drop delay ($DD_1$) of the cell particle B, of which speed ($v_0$) is less the maximum speed ($v_1$) of the standard bead A, can be calculated with the drop delay ($DD_0$) by the aforementioned equation (17) and can easily be used in the above sorting logic. For example, when $DD_0$=30, if ($t_0/t_1$)=0.95 then $DD_1$=31.58, and if ($t_0/t_1$)=1.05 then $DD_1$=28.57.

As discussed above, the position of each of the cell particles in the droplet flow DF close to the break-off point BP should exactly be determined in order to reliably sort them in accordance with the identification information. For example, suppose if the cell particle B moves to the position (PB) for a time corresponding to the delay time of the standard bead A, then the distance to the position (PB) can be expressed with the drop delay ($DD_0$) as follows.

$$PB = v_{1j}/T_0/\lambda = (t_0/t_1)*\lambda/\tau*T_0 \quad (18)$$
$$= (t_0/t_1)*DD_0$$

Therefore, the delay distance AD of the cell particle B behind the standard bead A is expressed with the drop delay ($DD_0$) as follows.

$$\Delta D = (t_0/t_1)*DD_0 - DD_0 = (t_0/t_1 - 1)*DD_0 \quad (19)$$

As the cell particle B generally has the speed slower than the standard bead A ($t_0 < t_1$), the delay distance $\Delta D$ has a negative value. For example, when $DD_0 = 30$ and $(t_0/t_1) = 0.95$, the cell particle B is behind the standard bead A by 1.5 times of $DD_0$. Similarly, the position of each of the cell particles can be determined at any timing including the delay time ($T_0$) with the drop delay ($DD_0$). Thus, the position of each of the cell particles is monitored or followed, so that the targeted cell particle TP is reliably charged through the charging electrode 36 for a given time (modulation period $\lambda$) and when determined as being at the appropriate position in the droplet flow $DF_1$.

What is claimed is:

1. A system for sorting biological particles in a liquid flow, each of the biological particles having a moving speed different from one another in the liquid flow, said system comprising:
   an optical mechanism emitting laser beam onto each of the biological particles to detect light therefrom;
   a controller determining the moving speed of each of the biological particles in the liquid flow in accordance with the light detected therefrom; and
   an electric charger charging each of the biological particles based upon the moving speed thereof.

2. The system according to claim 1, wherein the controller monitors, based upon the moving speed, a position of each of the biological particles within at least one droplet flow separating at a break-off point from the liquid flow, and the controller controlling the electric charger to charge each of the biological particles based upon the position thereof.

3. The system according to claim 2, wherein the controller collects identification information of each of the biological particles based upon the light detected therefrom, the controller controlling the electric charger to charge the biological particles with electricity of polarity selected in accordance with the identification information.

4. The system according to claim 3, wherein when a plurality of the biological particles having identification information different from one another are contained within the at least one droplet flow, the controller controls the electric charger not to charge the biological particles.

5. The system according to claim 3, wherein when a plurality of the biological particles having identification information same as one another are contained within the at least one droplet flow, the controller controls the electric charger to charge the biological particles.

6. The system according to claim 1, wherein when the moving speed of the biological particle is less than a predetermined threshold, the controller controls the electric charger not to charge the biological particle.

7. The system according to claim 1, the optical mechanism including,
   a first optical source emitting light onto the biological particle at a first position,
   a first optical detector receiving light from the biological particle emitted by the first optical source,
   a second optical source emitting light onto the biological particle at a second position, and
   a second optical detector receiving light from the biological particle emitted by the second optical source;
   wherein the controller calculates, in accordance with optical signals of the lights received from the first and second optical detectors, the moving time required for each of the biological particles to move between the first and second positions, so as to determine the moving speed of the biological particle.

8. The system according to claim 7, further comprising;
   a stationary imaging device taking an image of an imaging range covering the liquid flow and the break-off point,
   wherein the controller determines a flow distance between the first position and the break-off point, and a droplet-droplet distance between two adjacent droplets separated from the liquid flow, in accordance with the image taken by the stationary imaging device, the controller calculating a delay time required for the biological particle to move from the first position to the break-off point, based upon the flow distance, the droplet-droplet distance, and the moving time.

9. The system according to claim 7, wherein the light received from the biological particle, which is emitted by the first and second optical sources, is either one selected from a group of a forward-scattered light and a side-scattered light.

10. The system according to claim 7, wherein the lights emitted from the first and second optical sources onto the biological particle are laser beams having wavelength different to each other.

11. The system according to claim 1, further comprising:
    a sheath container for receiving a sheath liquid;
    a plenum container for supplying the sheath liquid to the sheath container via an extension tube;
    a first pressure source connected to the plenum container;
    a sample container for receiving a sample liquid containing the biological particles;
    a second pressure source connected to the sheath container;
    a flow cell in fluid communication with the sheath container and the sample container, defining the liquid flow which encompasses the sample liquid with the sheath liquid, and
    a sheath temperature controller for controlling temperature of the sheath liquid so as to keep it stable.

12. The system according to claim 11, wherein the sheath temperature controller includes an insulation jacket provided around the extension tube.

13. The system according to claim 11, wherein the sheath temperature controller stabilizes the temperature of the sheath container.

14. The system according to claim 13, wherein the sheath temperature controller controls the temperature of the sheath container in a range between 4-42 degrees centigrade.

15. The system according to claim 11, further comprising:
    a sample temperature controller controlling temperature of the sample liquid so as to keep it in a thermal range where the biological particles can survive,
    wherein the sheath temperature controller keeps the sheath fluid in the thermal range where the biological particles can survive as well.

16. The system according to claim 1, wherein a biological particle moving further away from a center of the flow call has a slower moving speed than a biological particle moving along the center of the flow cell.

17. A process for sorting biological particles in a liquid flow, each of the biological particles having a moving speed different from one another, said process comprising:

emitting laser beam onto each of the biological particles to detect light therefrom;

determining the moving speed of each of the biological particles in the liquid flow in accordance with the light detected therefrom; and charging each of the biological particles based upon the moving speed thereof.

18. The process according to claim 17, wherein the step of charging includes, monitoring, based upon the moving speed, a position of each of the biological particles within at least one droplet flow separating at a break-off point from the liquid flow, and controlling the electric charger to charge each of the biological particles based upon the position thereof.

19. The process according to claim 18, wherein the step of charging, collecting identification information of each of the biological particles based upon the light detected therefrom, and charging the biological particles with electricity of polarity selected in accordance with the identification information.

20. The process according to claim 19, wherein the step of charging includes failing to charge a plurality of the biological particles within the at least one droplet flow, when the biological particles within the at least one droplet flow have identification information different from one another.

21. The process according to claim 19, wherein the step of charging includes charging a plurality of the biological particles within the at least one droplet flow, when the biological particles within the at least one droplet flow have identification information same as one another.

22. The process according to claim 17, wherein the step of charging includes failing to charge the biological particle when the moving speed of the biological particle is less than a predetermined threshold.

23. The process according to claim 17, further comprising:

emitting light onto the biological particle at first and second positions, and receiving light from the biological particle at first and second positions, calculating, in accordance with optical signals of the lights received from the first and second optical detectors, the moving time required for each of the biological particles to move between the first and second positions, so as to determine the moving speed of the biological particle.

24. The process according to claim 23, further comprising:

taking an image of an imaging range covering the liquid flow and the break-off point, determining a flow distance between the first position and the break-off point, and a droplet-droplet distance between two adjacent droplets separated from the liquid flow, in accordance with the image taken by the stationary imaging device, and calculating a delay time required for the biological particle to move from the first position to the break-off point, based upon the flow distance, the droplet-droplet distance, and the moving time.

25. The process according to claim 17, wherein a biological particle moving further away from a center of the flow call has a slower moving speed than a biological particle moving along the center of the flow cell.

* * * * *